United States Patent
Xu et al.

(10) Patent No.: US 6,822,225 B2
(45) Date of Patent: Nov. 23, 2004

(54) PULSED DISCHARGE IONIZATION SOURCE FOR MINIATURE ION MOBILITY SPECTROMETERS

(75) Inventors: Jun Xu, Knoxville, TN (US); J. Michael Ramsey, Knoxville, TN (US); William B. Whitten, Oak Ridge, TN (US)

(73) Assignee: UT-Battelle LLC, Oak Ridge, TN (US)

( * ) Notice: Subject to any disclaimer, the term of this patent is extended or adjusted under 35 U.S.C. 154(b) by 1 day.

(21) Appl. No.: 10/254,749

(22) Filed: Sep. 25, 2002

(65) Prior Publication Data

US 2004/0164238 A1 Aug. 26, 2004

(51) Int. Cl.[7] ............................................. G01D 55/44
(52) U.S. Cl. .......................... 250/287; 250/288; 250/282
(58) Field of Search .................................. 250/287, 288, 250/282, 299

(56) References Cited

U.S. PATENT DOCUMENTS

| | | | | |
|---|---|---|---|---|
| 4,283,291 A | * | 8/1981 | Lowther | 422/186.15 |
| 5,304,797 A | * | 4/1994 | Irie et al. | 250/287 |
| 5,405,781 A | * | 4/1995 | Davies et al. | 436/52 |
| 5,684,300 A | | 11/1997 | Taylor et al. | |
| 5,789,745 A | * | 8/1998 | Martin et al. | 250/286 |
| 6,225,623 B1 | | 5/2001 | Turner et al. | |

FOREIGN PATENT DOCUMENTS

WO    WO 93/11554    6/1993

* cited by examiner

*Primary Examiner*—Nikita Wells
*Assistant Examiner*—Anthony Quash
(74) *Attorney, Agent, or Firm*—Quarles & Brady LLP

(57) ABSTRACT

A method and apparatus is disclosed for flowing a sample gas and a reactant gas (38, 43) past a corona discharge electrode (26) situated at a first location in an ion drift chamber (24), applying a pulsed voltage waveform comprising a varying pulse component and a dc bias component to the corona discharge electrode (26) to cause a corona which in turn produces ions from the sample gas and the reactant gas, applying a dc bias to the ion drift chamber (24) to cause the ions to drift to a second location (25) in the ion drift chamber (24), detecting the ions at the second location (25) in the drift chamber (24), and timing the period for the ions to drift from the corona discharge electrode to the selected location in the drift chamber.

16 Claims, 4 Drawing Sheets

PULSED DISCHARGE IONIZATION SOURCE FOR MINIATURE ION MOBILITY SPECTROMETERS

STATEMENT REGARDING FEDERALLY SPONSORED RESEARCH

This invention was made under Contract DE-AC05-00OR22725 between the U.S. Department of Energy and the assignee of the present invention. The Government has certain rights in this invention.

BACKGROUND OF THE INVENTION

The field of the invention is ion mobility spectrometers. Ion mobility spectrometry (IMS) is an important method for detecting drugs, explosives, VOCs, and chemical warfare agents at ambient pressure. Explosives generally have high electron affinities and drugs and chemical warfare (CW) agents have high proton affinities. When these chemicals enter the reactor of an ion mobility spectrometer (IMS), negative and positive ions of these samples will be preferentially formed. Such a preference allows a high sensitivity of IMS technology in detecting trace explosives, drugs, and CW agents. Some commercial ion mobility spectrometers are available for detecting the above chemicals.

Miniaturization of such instruments provides advantageous applications in the field. However, a typical problem for commercial hand-held IMS is loss of sensitivity. For example, the sensitivity of a desktop size IMS detector now used in airports, is about 1 nanogram for explosives. The sensitivity of a smaller, handheld version, would be reduced more than 100 times. The main reason for the reduced sensitivity is the use of a nickel-63 ($Ni^{63}$) radioactive source for ionization. Nickel-63 emits electrons with 67 keV kinetic energy. The low stopping power of the high-energy electrons in gases generates less ions in the small volume of the miniature IMS ionization chamber, resulting in the low sensitivity. In addition, a nickel-63 source has potential hazards due to its radioactive nature. An example of an ion-producing device with a nickel-63 radioactive source is disclosed in Turner et al., U.S. Pat. No. 6,225,623, issued May 1, 2001. For general information concerning the principles of ion mobility spectrometry, reference is made to Eiceman, G. A. and Karpas, Z., "Ion Mobility Spectrometry," CRC Press, Boca Raton Fla., USA, 1994.

In Taylor et al., U.S. Pat. No. 5,684,300, issued Nov. 4, 1997, and PCT Pub. No. WO 03/11554, published June 10, 1993, pulses with various polarities, amplitudes, and widths are generated by a RF oscillator and are used to produce ions through a corona discharge. Certain features of these pulses are undefined, which tends to limit the performance of this kind of spectrometer. An ion gate is used to control ions entering an ion mobility channel and the electronics require that the device have extra size.

SUMMARY OF THE INVENTION

The invention is a method and apparatus for providing a pulsed discharge ionization source particularly designed for miniature ion mobility spectrometers (IMS), but also usable in other analytical instruments. The invention uses a pulse to generate a corona around a tip of non-radioactive (non-doped) material to generate ions from a sample gas and to signal the start of ion motion.

In a further aspect of the invention, the applied potential comprises a pulse component and a dc base voltage component, which reduces the pulse component. This reduces noise and power consumption.

Miniaturized ion mobility spectrometers equipped with the pulsed discharge ionization source of the present invention have the following advantages: (1) high sensitivity because the ions are concentrated in a very small volume, (2) the use of an ion gate and its associated electronics is unnecessary, and (3) a high dynamic range is available because the ionization rate can be adjusted. The present invention provides a method and an apparatus in which ions are generated in a highly confined space and time, which results in high sensitivity for miniature IMS detectors. A processor-based electronic control enables timing of the initial ion motion with the ionization pulse. This provides a device without the need for an ion extract gate for ions entering a drift chamber. This reduces the size of the drift chamber body, the electronics control package, and power consumption. The invention also provides for increased dynamic range by adjusting the pulse height or by adjusting the DC bias.

Other objects and advantages of the invention, besides those discussed above, will be apparent to those of ordinary skill in the art from the description of the preferred embodiments which follows. In the description reference is made to the accompanying drawings, which form a part hereof, and which illustrate examples of the invention. Such examples, however are not exhaustive of the various embodiments of the invention, and therefore reference is made to the claims which follow the description for determining the scope of the invention.

DETAILED DESCRIPTION OF THE PREFERRED EMBODIMENTS

Figure 1:
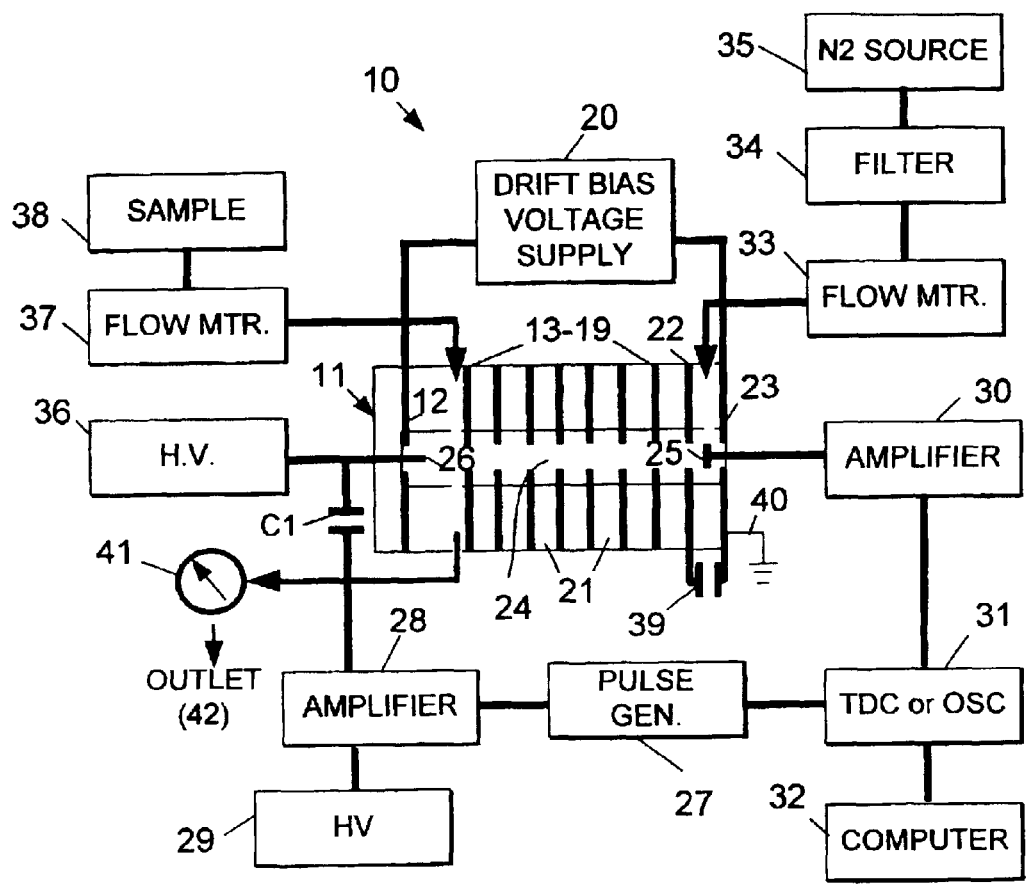
FIG. 1 is a schematic view of a first embodiment of an apparatus for practicing the method of the present invention.

Referring to FIG. 1, the present invention is practiced in a miniature ion mobility spectrometer (IMS) 10 employing a pulsed corona discharge ion source as shown in FIG. 1.

Figure 2:
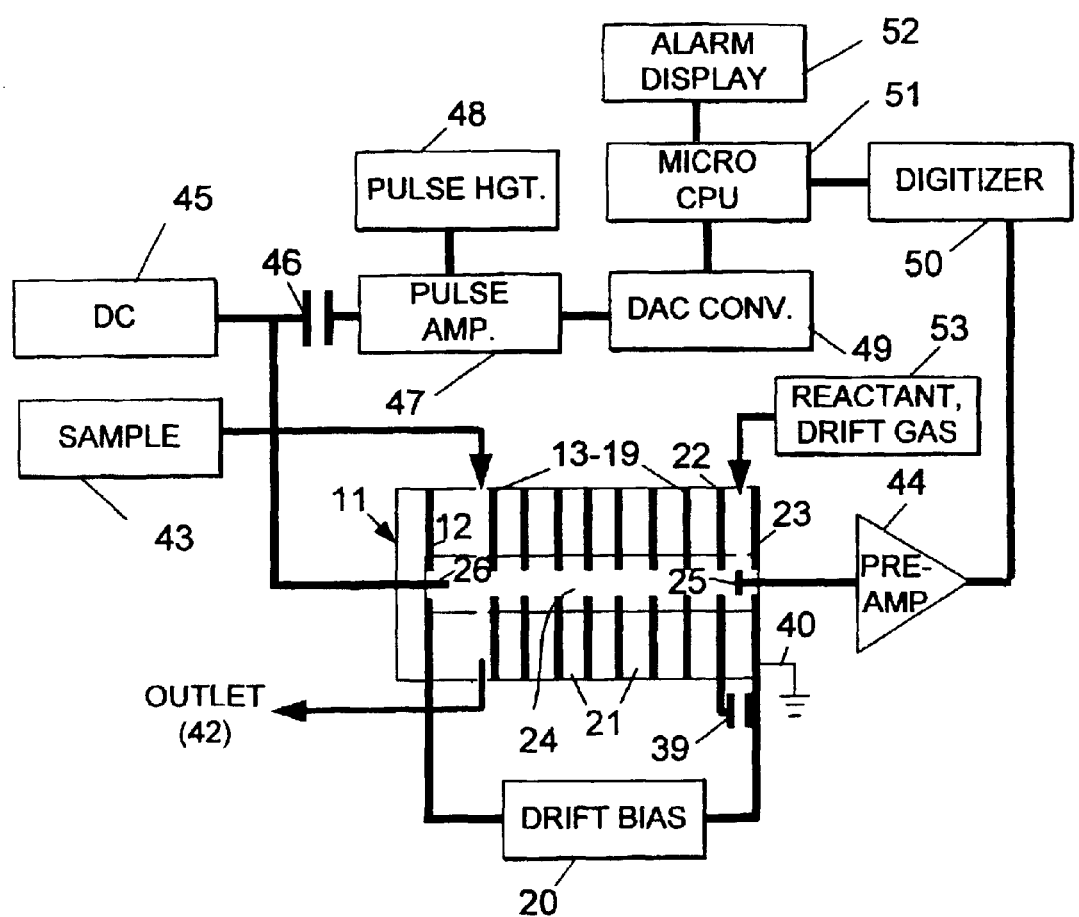
FIG. 2 is a schematic view of a second embodiment of an apparatus for practicing the method of the present invention.

FIG. 2 shows a second miniaturized embodiment of the apparatus featuring a microelectronic CPU 51.

In FIGS. 1 and 2, the device has a cylindrical body 11 comprised of ten (10) stacked, annular metal electrodes 12–19, 22 and 23 which are separated by annular spacers 21 (5-mm thick and 8 mm ID) of a dielectric material such as Teflon. This forms a drift channel 24 which can be in the range from 1.7 mm–2.5 mm in diameter and 35–50 mm in effective length. In FIG. 1, the drift channel is specifically 2.5 mm in diameter and 47 mm in length, respectively.

Nine miniature resistors (not shown), each with 2 MΩ resistance, 1% tolerance, are connected between the electrodes 12–19, 22 and 23 to form a voltage divider. The first electrode 12 is biased with a power supply 20 to provide an ion drift voltage, with the voltage being distributed to the intermediate electrodes 13–19, 22 and 23 through these resistors. The last electrode 23 is connected to an electrical ground 40. The next to the last electrode 22 is connected to a 470-pf capacitor 39 to suppress transients. An ion detector electrode 25 is located in the drift chamber 24 between the last electrode 23 and the next to last electrode 22. Positive or negative potentials can be applied to the detection electrode 25 for detecting positive and negative ions, respectively.

Figure 5:
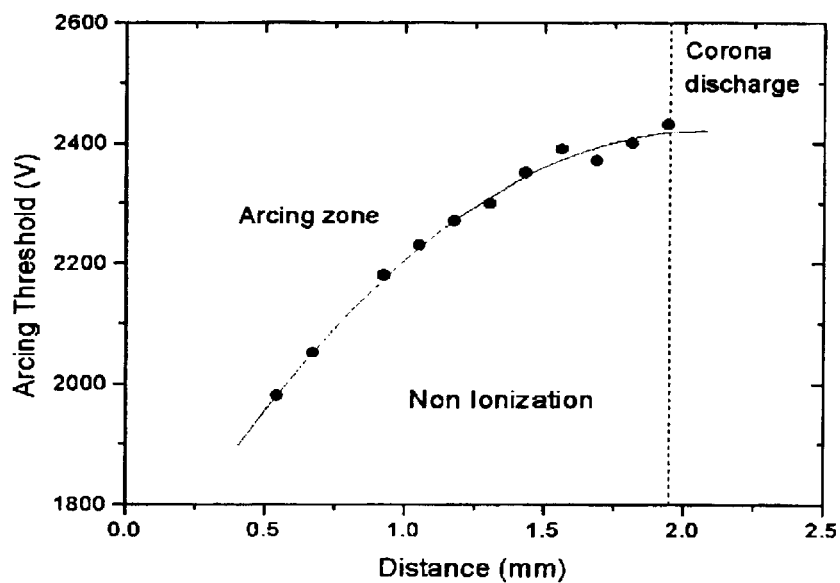
FIG. 5 is a graph of arcing threshold voltage vs. distance between two electrodes for generating an ion-producing corona.

A nickel-tipped electrode 26 of non-radioactive (non-doped) material with an end radius of curvature of approximately 25 µm is mounted at the entrance of the drift chamber 24. The second drift channel electrode 13 is used as the counter electrode for corona discharge with the distance to the tip 26 being larger than the threshold distance for discharge zone as illustrated in FIG. 5. The corona-producing tip 26, together with the second electrode 13 of the IMS channel, formed a tip-ring corona discharge element.

A sample gas is supplied from reservoir 38 in FIG. 1 through a flow meter 37 to an inlet into the corona discharge end of the drift chamber 24. A carrier gas, in this case, nitrogen, is supplied from a source 35 through a filter 34 and a second flow meter 33 to an inlet into the detection end of the drift chamber 24. These gases exit the drift chamber through valve 41 and outlet 42. In FIG. 2, where parts similar to FIG. 1 have the same number, a sample gas is received from a source 43, while dry air enters from a supply 53 into an entrance at the opposite end of the drift chamber 24. The dry air includes both drift gas and reactant gas. All of these gases exit from exit 42.

A corona is produced at the electrode 26 by applying an electrical pulse having a width of from 40 ns to 100 µs, a pulse height varying from 0.2–3.3 kV and a repetition rate (frequency) of 20 Hz. The pulse is generated as a base dc voltage component originating at a high voltage source 36 and a varying pulse component generated by a pulse generator comprising high voltage source 29, amplifier 28 and pulse generator 27, which generates pulses on the order of 5 volts before they are amplified. These pulses are summed with a base dc voltage through capacitor C1. The resulting amplified high-voltage pulse is applied to the corona tip electrode 26, which is seen in FIG. 1. During the high voltage pulse, ions are generated in the vicinity of the tip 26. After the pulse, the ions move along the drift channel 24 through the carrier gases under the influence of the drift field bias provided by voltage supply 20.

The corona discharge pulse also provides a start signal for timing the ion mobility movements. For each pulse, ions are separated according to their travel time to reach the ion detector 25 located at the end of the channel 24. There, an ion current is produced and is transmitted to a current amplifier 30 connected to electrode 25. The time difference between the start signal and arrival of ions is detected by a time-to-digital converter (TDC) 31 and is transmitted to a computer 32 for analysis. If a digital oscilloscope 31 is used instead of time-to-digital converter 31, the start pulse triggers the oscilloscope. The ion arrival signal is recorded by the scope and sent to the computer 32.

The detector 25 is connected to an amplifier 30 in FIG. 1 which amplifies the signals. The oscilloscope is connected to an Apple Macintosh computer 32 running a Labview application program in FIG. 1. This is a lab prototype embodiment for demonstrating the operation of the invention. In FIG. 2, the components in FIG. 1 are designed for reduced size in a commercial embodiment.

Ion mobility spectra of both positive and negative ions were measured as a function of pulse width. For positive ions, the ion current increased with pulse width and saturated. For negative ions, the ion current peaked rapidly and then decayed with increased pulse width.

Figure 3:
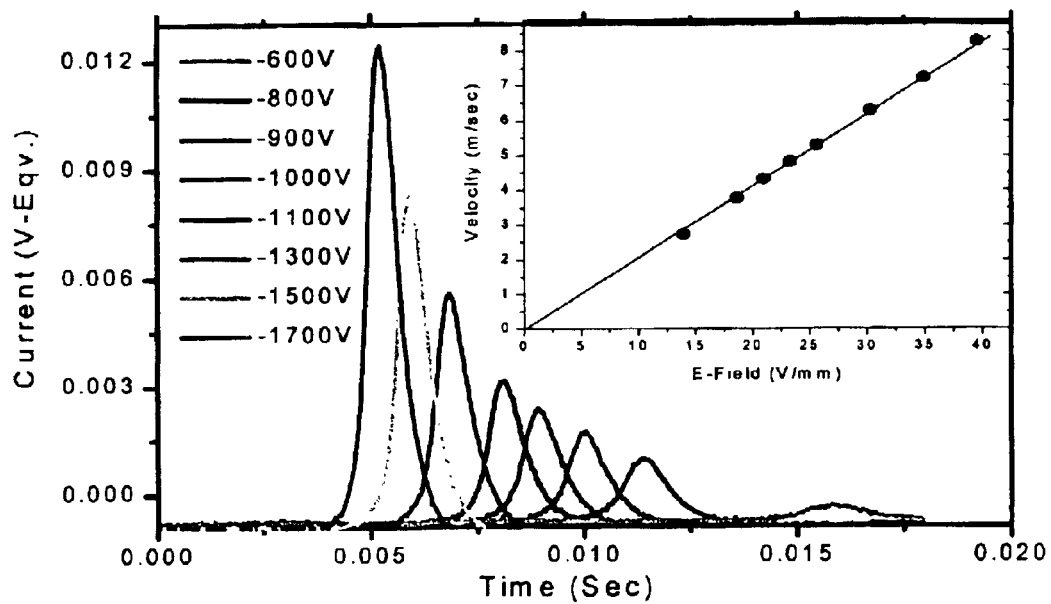
FIG. 3 is a graph of ion detection current vs. time vs. dc bias voltage.

Ion mobility spectra of negative ions produced by pulsed corona discharge and by ionization of air were measured as a function of drift bias voltage from −600 VDC to −1700 VDC as seen in FIG. 3. The pulses had 1.08 µs width and +2600V amplitude. The sample air was at atmospheric pressure and room temperature. The drift gas was $N_2$, which was fed from a source 35 through a filter 34 and flow meter 33 at the detector end of the IMS channel 24 with a flow rate of 20 sccm (standard cubic centimeter per minute).

Figure 4:
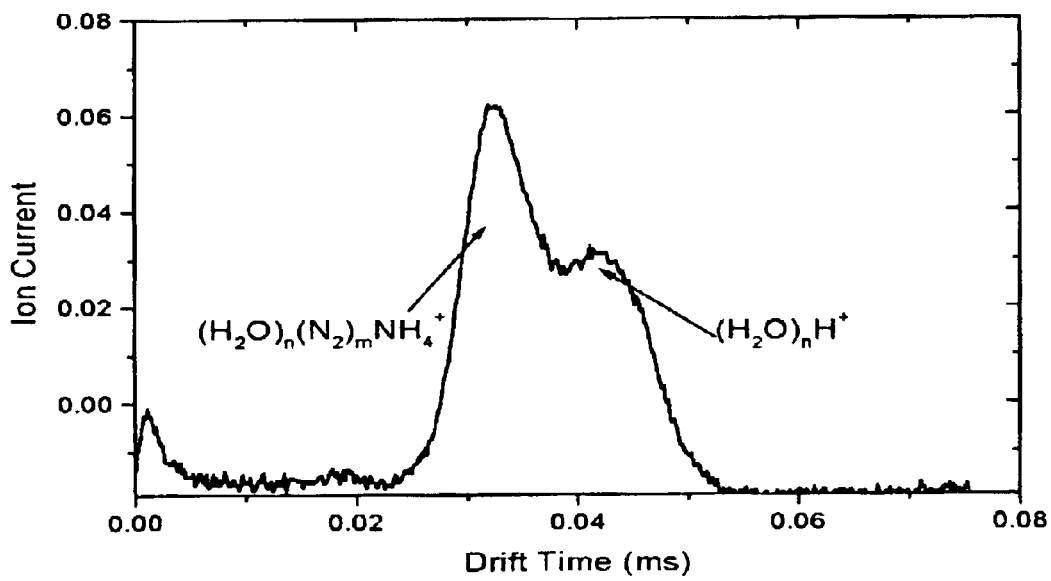
FIG. 4 is a graph of ion detection current vs. drift time for moist air and for nitrogen supplied to the drift chamber.

A typical mobility spectrum of positive ions generated by pulsed corona discharge ionization of air is shown in FIG. 4. For producing positive ions, the pulse potential applied to the tip 26 was also positive, the same polarity as used for generating negative ions, with a height of 3100 VDC and a width of 14.5 µs.

The corona discharge properties depend on the distance between the tip 26 and the counter electrode 13. The counter electrode can be either a ring or a tip. This is illustrated in FIG. 5. For distances less than 1.96 mm, no ionization occurred until a threshold of potential, about 1900 VDC was reached. At and above the threshold, spark breakdown occurred, which preceded the establishment of a stable corona. The voltage threshold was found to increase as a function of distance, as shown in FIG. 5, up to 2400 volts at 1.96 mm. Stable corona discharge conditions could not be found in this distance range. When the distance was larger than 1.96 mm, corona discharge occurred at a threshold that was a function of the drift bias.

Figure 6:
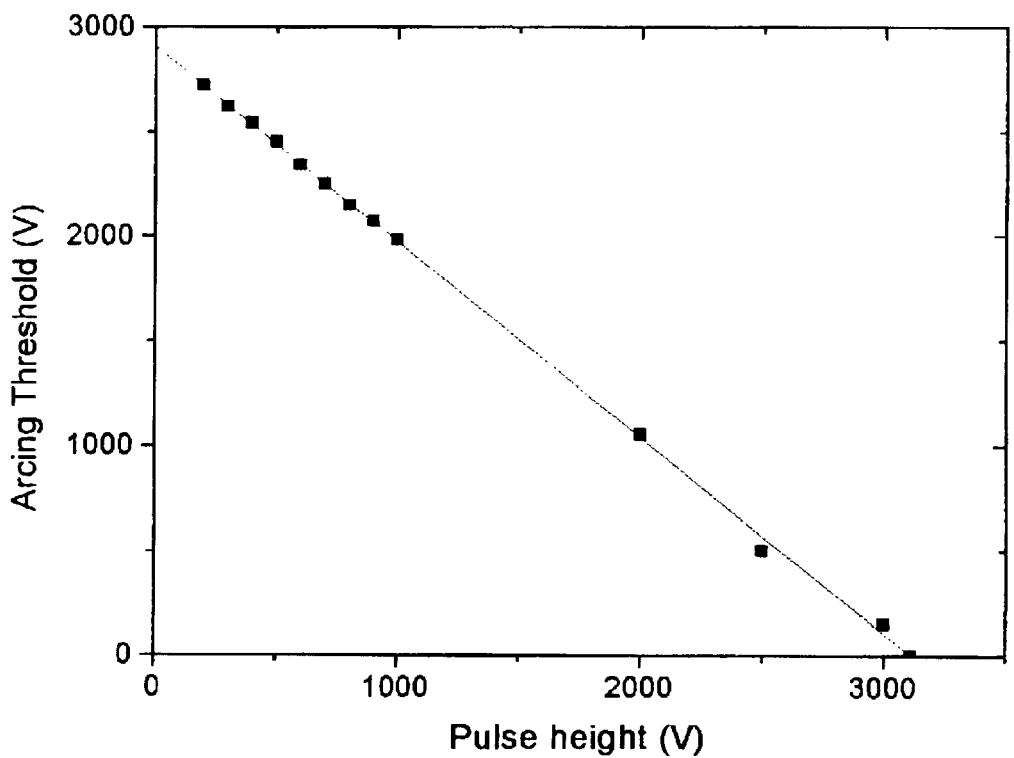
FIG. 6 is a graph of arcing threshold voltage vs. pulse height for generating an ion-producing corona.

Corona discharge was also generated by a combination of a base dc potential in combination with a pulsed voltage potential. As seen in FIG. 1, a dc voltage supply 36 is connected to a dc pulse generator 27, an amplifier 28 and a second dc supply 29 through capacitor C1. As seen in FIG. 2, dc voltage supply 45 is connected to a pulse amplifier 47 and a pulse height control circuit 48 through a capacitor 46. In FIG. 2, the pulse is commanded by the microelectronic CPU 51 through a digital-to-analog converter 49. The base dc potential, which varied from 0 to 3000 volts, was superimposed on the pulsed potential. The combined potentials permit independent variation of the dc potential, pulse height, and pulse width to the corona tip. For a given pulse height, the ion mobility spectrum current can be measured as a function of dc bias voltage. For a higher pulse voltage, the current exhibited a threshold for the dc bias and increased to a saturation level. The dc threshold was found to linearly decrease from 3000 VDC to 200 VDC as the pulse height was increased from 200 VDC to 3000 VDC, as shown in FIG. 6. Therefore, ions could be generated with lower voltage pulses if the dc base voltage were raised. The detector 25 in FIG. 2 is connected in close proximity to an amplifier 44 which amplified the small signal. This signal is then digitized by digitizer 50 to filter noise, and is then read by the microelectronic CPU 51. For a specific substance, thresholds are set, and if a threshold is exceeded, a visual indication is provided to a user through an alarm display 52, such as by illuminating an icon or changing the color of an object on a display screen. The electronic circuits 20 and 44–52 in FIG. 2 can be made quite compact and can be mounted on circuit boards. These can be packaged with the drift chamber body 11 in a package the size of a lightweight notebook computer of the type having a titanium case.

The pulsed corona ionization source of the present invention eliminates the need for the ion gate of the prior art near the ion source. It also provides for a smaller drift chamber and a smaller body for housing the drift chamber. The invention also provides a method for timing the movement of the ions between the source and the detector. The use of a dc voltage comprising a pulse element and a base voltage element reduces the pulse component, which reduces noise and power consumption.

This has been a description of detailed examples of the invention. It will apparent to those of ordinary skill in the art that certain modifications might be made without departing from the scope of the invention, which is defined by the following claims.

We claim:

1. A method of pulsed discharge for an analytical instrument, comprising:

flowing a sample gas and a reactant gas past a corona discharge electrode of non-radioactive material situated at a first location in an ion drift chamber;

applying a pulsed voltage to the corona discharge electrode to cause a corona which in turn produces ions from the sample gas and the reactant gas;

applying a dc bias to the ion drift chamber to cause the ions to drift to a second location in the ion drift chamber through a medium provided by a drift gas without assistance of an ion gating structure;

detecting the ions at the second location in the drift chamber;

timing a period for the ions to drift from the corona discharge electrode to the second location in the drift chamber; and using the timed period to determine an identity of the sample gas.

2. The method of claim 1, wherein applying the pulsed voltage to the corona discharge electrode further includes generating a pulsed voltage comprising a controllable base dc component and a controllable varying pulse component.

3. The method of claim 1, wherein said pulsed voltage has a selected pulse width within a range from 40 ns to 100 $\mu$s.

4. The method of claim 1, wherein said pulsed voltage has a selected pulse height in a range from 0.2–3.3 kV.

5. The method of claim 1, wherein said pulse voltage has a frequency of approximately 20 Hz.

6. The method of claim 1, further comprising flowing the drift gas into the drift chamber proximate to the second location in the drift chamber.

7. The method of claim 1, further comprising recording the time at which ions from the sample gas arrive at the detector, comparing ions from the sample gas detected at the detector with a threshold, and when the threshold is exceeded, providing a visual display to a user indicating detection of a substance associated with the threshold.

8. An analytical instrument comprising:

a body forming an elongated chamber for reaction of gases and for movement of gases, said chamber having a first entrance for receiving a sample gas and having a second entrance for receiving a reactant gas and a drift gas;

a corona discharge electrode of non-radioactive material and a counter electrode positioned in the body at a first location in the chamber in a path of flow for the sample gas;

an ion detector at a second location the chamber spaced from the corona discharge electrode;

wherein a pair of electrodes are provided for applying a dc bias voltage along a length of the chamber; and an electronic control for controlling application of a voltage to the corona discharge electrode and for timing an interval beginning with the application of the corona discharge voltage and ending with detection of the ions at the ion detector; and wherein the instrument does not have an ion control gate and does not confine the ions produced by corona discharge element at an end of the drift chamber where ions are produced.

9. The instrument of claim 8, wherein the body forming the chamber has at least four electrode rings spaced apart and separated by dielectric spacer rings, said electrode rings and spacer rings having central openings which together form at least a portion of the chamber.

10. The instrument of claim 8, wherein the corona discharge electrode is disposed either axially or transversely to the elongated chamber through an opening in an end electrode and has a tip that is spaced from a next to the last electrode ring, which forms the counter electrode for the corona discharge element.

11. The instrument of claim 8, wherein the electronic control is operable for applying a voltage to the corona discharge electrode which further comprises a controllable base dc component and a controllable varying pull component.

12. The instrument of claim 8, wherein the electronic control further comprises means for applying a voltage to the corona discharge electrode which further comprises a base dc component and a varying pulse component.

13. The instrument of claim 8, further comprising means for flowing a second gas into the drift chamber proximate to the second location in the drift chamber and means for flowing a reactant gas into the chamber.

14. The instrument of claim 8, wherein the electronic control further comprises a microelectronic CPU for generating a start pulse, said CPU being connected to the detector through an amplifier and to a digitizer to receive detected ion signals.

15. The instrument of claim 14, wherein the electronic control is connected to a visual display, and wherein the electronic control identifies sample gas by timing an ion drift time and compares ions detected at the detector with a threshold, and when the threshold is exceeded, provides a signal to a user through the visual display to indicate detection of a substance associated with the threshold.

16. An analytical instrument comprising:

a body forming an elongated chamber for reaction of gases and for movement of gases, said chamber having a first entrance for receiving a sample gas and having a second entrance for receiving a reactant gas and a drift gas;

a corona discharge electrode of non-radioactive material and a counter electrode positioned in the body at a first location in the chamber in a path of flow for the sample gas;

an ion detector at a second location the chamber spaced from the corona discharge electrode;

wherein a pair of electrodes are provided for applying a dc bias voltage along a length of the chamber; and an electronic control further comprising a microelectronic CPU for controlling application of a controllable base dc component and a controllable varying pulse component to the corona discharge electrode;

wherein the microelectronic CPU times an interval beginning with the application of the corona discharge voltage and ending with detection of the ions at the ion detector;

wherein the microelectronic CPU controls application of a dc bias voltage to the pair of electrodes for applying the dc bias voltage along a length of the chamber; and wherein the instrument does not have an ion control gate at an end of the drift chamber where ions are introduced.

* * * * *

UNITED STATES PATENT AND TRADEMARK OFFICE
CERTIFICATE OF CORRECTION

PATENT NO.    : 6,822,225 B2
DATED         : November 23, 2004
INVENTOR(S)   : Xu et al.

It is certified that error appears in the above-identified patent and that said Letters Patent is hereby corrected as shown below:

Column 6,
Line 15, "pull" should be -- pulse --.

Signed and Sealed this

Twenty-fourth Day of May, 2005

JON W. DUDAS
*Director of the United States Patent and Trademark Office*